United States Patent [19]

Vedros

[11] Patent Number: 5,198,217
[45] Date of Patent: Mar. 30, 1993

[54] TOPICAL DEMULCENT FOR VIRAL AND INFLAMMATORY DISEASES OF THE SKIN

[75] Inventor: Neylan A. Vedros, Alameda, Calif.

[73] Assignee: Choice Pharmaceuticals, San Leandro, Calif.

[21] Appl. No.: 764,486

[22] Filed: Sep. 24, 1991

[51] Int. Cl.$^5$ .................... A61K 35/78; A61K 31/715
[52] U.S. Cl. .................................. 424/195.1; 514/54; 514/738
[58] Field of Search ................ 424/195.1; 514/54, 738

[56] References Cited

U.S. PATENT DOCUMENTS

| | | | |
|---|---|---|---|
| 2,276,241 | 3/1942 | Shelton | 514/25 |
| 4,381,296 | 4/1983 | Tinnell | 424/659 |
| 4,874,794 | 10/1989 | Katz | 514/724 |

OTHER PUBLICATIONS

Alarcon, B., et al., Antiviral Res. 4:231-243 (1984).
Baba, M., and Shigeta, S., Antiviral Res. 7:99-107 (1987).
Deig, E. F., et al., Antimicrob. Agents and Chemother. 6(4):524-525 (1974).
Ehresmann, D. W., et al., "Characterization of the Anti--Herpesvirus Activity in Extracts of Marine Algae," Abstract from the Annual Meeting of the American Society for Microbiologists, 1975.
Ehresmann, D. W., et al., J. Phycol. 13:37-40 (1977).
Fukuchi, K., et al., Antiviral Res. 11:285-298 (1989).
Hattori, T., et al., Antiviral Res. 11:255-262 (1989).
Entries for Carrageenan, Tannic Acid, and Licorice Root, in *Encyclopedia of Common and Natural Ingredients*, Albert Y. Leung, ed.
Pompei, M., et al., Nature 281:689 (1979).
Entry for Carrageenan, in *The Merck Index*, p. 238, M. Windholz, ed., 1976.
Chapter 11, pp. 133-147, "Antiviral Triterpenoids in Cultured Cells".
"II. Tannins," pp. 159-165.

*Primary Examiner*—John W. Rollins
*Attorney, Agent, or Firm*—Peter J. Dehlinger; Gary R. Fabian

[57] ABSTRACT

The composition of the present invention is a topical protectant and can be used in a method for the relief of discomfort due to cold sores (Herpes virus outbreaks). The combination of ingredients softens and soothes the cold sore, preventing cracking, and is most effect when the recurrent herpes infection just begins (mild burning and itching). The composition of the present invention can also be applied for the treatment of skin irritations due to chapping, sunburn, windburn, scrapes, abrasions, cracked lips, or other skin disorders.

13 Claims, 1 Drawing Sheet

Inhibition of Herpes simplex 1

TOPICAL DEMULCENT FOR VIRAL AND INFLAMMATORY DISEASES OF THE SKIN

FIELD OF THE INVENTION

The present invention describes a composition, comprising tannic acid, licorice root extract, and carrageenan, which acts as a topical demulcent for the relief of discomfort due to skin diseases and disorders. The present invention further describes methods of treatment for such skin disorders.

REFERENCES

Baba et al., Antiviral Research, 7:99 (1987).
Deig, E. F., et al., Antimicrob. Agents and Chemoth. 6(4):524-525 (1974).
Erhsmann et al., J. Phycol. 13:37 (1977).
Fukuchi et al., Antiviral Res. 11:285 (1989).
Jekel, U.S. Pat. No. 2,970,032.
Katz, U.S. Pat. No. 4,874,794.
Nichols, U.S. Pat. No. 2,095,571.
Nieman, K., Chem. Weekblad. 48:213 (1952).
Pratt, R., and Youngken, H. W., Pharmacognsy, Second edition, Lippincott, Philadelphia, Penna. (1956).
Prehn, U.S. Pat. No. 2,175,780.
Remington's Pharmaceutical Sciences, 15th Ed., pg. (1975).
Shelton, U.S. Pat. No. 2,276,241.
Su, J. C., et al., Biochemistry 1:168-171 (1962).
Tinnel, U.S. Pat. No. 4,381,296.

BACKGROUND OF THE INVENTION

Dermatological manifestations are considered to be on the most common causes of morbidity in humans. Included are any insult to the skin and ranging from minor abrasions, sunburn, to the severe fungal and viral lesions. The incidence of the majority of the minor skin afflictions are difficult to determine since patients rarely seek medical treatment.

Most viral infections of the skin are caused by the Herpes viruses. The most common of these is *Herpes labialis* (cold sores or fever blisters) caused by Herpes simplex (estimated cases per annum in the U.S. of the recurrent infections are 100,000,000). Genital infections are caused by Herpes Simplex I (estimated cases per annum in the U.S. of recurrent infections are 20,000,000) and is the third most important sexually transmitted disease. Chicken pox is caused by *Varicella zoster virus* (estimated cases per annum in the U.S. are 3,800,000) and the latent form of this virus (*Herpes zoster*) causes shingles and the estimated cases per annum in the U.S. are 2,000,000. Dermatophyte infections are also very common but the incidence in the U.S. is not known.

Treatment for the minor skin afflictions generally involve mixtures of camphor, menthol, acids, phenol, lanolin, or high concentrations of alcohol. Some include the pain killer lidocaine. The following references teach some of these treatments and methods:

1. Nichols described an alcohol-glycerine solution of salicylic acid and boric acid for treatment of ringworm (athlete's foot).

2. Prehn described a salicylic acid menthol and camphor mixture in a boric acid and starch vehicle for treatment of fungus infections and dermatitis.

3. Shelton described a tannin, phenolic and boric acid mixture for treatment of various skin infections.

4. Jekel described a tannin boric acid product for treatment of various dermatophyte infections.

For the treatment of viral infections treatments have been described that consist of using either (i) a combination of acids, where the acids are at high concentrations, or (ii) long chain aliphatic alcohols. The following references describe some such treatments for viral skin diseases:

1. Tinnel described a mixture of boric acid, salicyclic acid, and tannic acid (2-12:2-12:1-6%) specifically for the treatment of Herpes infections. Two examples in this reference (Nos. 8 and 13) describe the treatment of genital Herpes on the vulva with very high concentration acid mixtures (15% boric acid, 7% salicylic acid, and 15% tannic acid) in an ethanol carrier.

2. Katz described a composition of C-20 to C-26 aliphatic alcohols in a variety of carriers for the treatment of viral and inflammatory diseases of the skin.

In vitro inhibition of Herpes viruses by chemically defined plant extracts (Fukuchi et al.), marine algae (Erhsmann et al., 1977), and glycyrrhizin, from the licorice plant (Baba et al., 1987), has also been shown.

Experiments performed in support of the present invention have lead to the discovery of a topical spray that is efficacious in the treatment of minor skin afflictions and Herpes infections. The composition of the present invention contains no alcohols, corticosteroid or -caines (e.g., lidocaine).

SUMMARY OF THE INVENTION

The present invention includes a composition that is suitable for providing a topical dermatological spray, comprising tannic acid, licorice root extract, carrageenan, and a pharmacologically acceptable fluid carrier. In this composition preferred concentration ranges for the above components include the following: tannic acid, approximately 0.8% to 1.5% w/v; licorice root extract, approximately 0.025% to 0.75% w/v; and, carrageenan, approximately 0.1% to 1.5% w/v.

The pharmacologically acceptable fluid vehicle may consist of a variety of components. Two preferred components for the fluid vehicle are glycerin and pectin. The fluid vehicle may also include the addition of preservatives, such as sodium benzoate.

One preferred formulation of the composition of the present invention consists essentially of glycerin, 20% v/v; pectin, 1.0% w/v; licorice root extract, 0.025% w/v; tannic acid, 1.0% w/v; carrageenan, 0.1% w/v; sodium benzoate, 0.25% w/v; and distilled water.

The composition of the present invention can be used in a method of treating skin disorders and inflammations. In this method the composition is topically applied to the affected area of skin or membrane. The method of the present invention can be used to treat a wide variety of viral and inflammatory skin disorders including: Herpes Zoster, bee stings, bug bites, eczema, psoriasis, apthos ulcers/canker sores, oral/labial herpes, genital herpes, pharyngitis/tonsillitis and dermatitis.

DETAILED DESCRIPTION OF THE INVENTION

I. The Composition of the Invention

Figure 1:
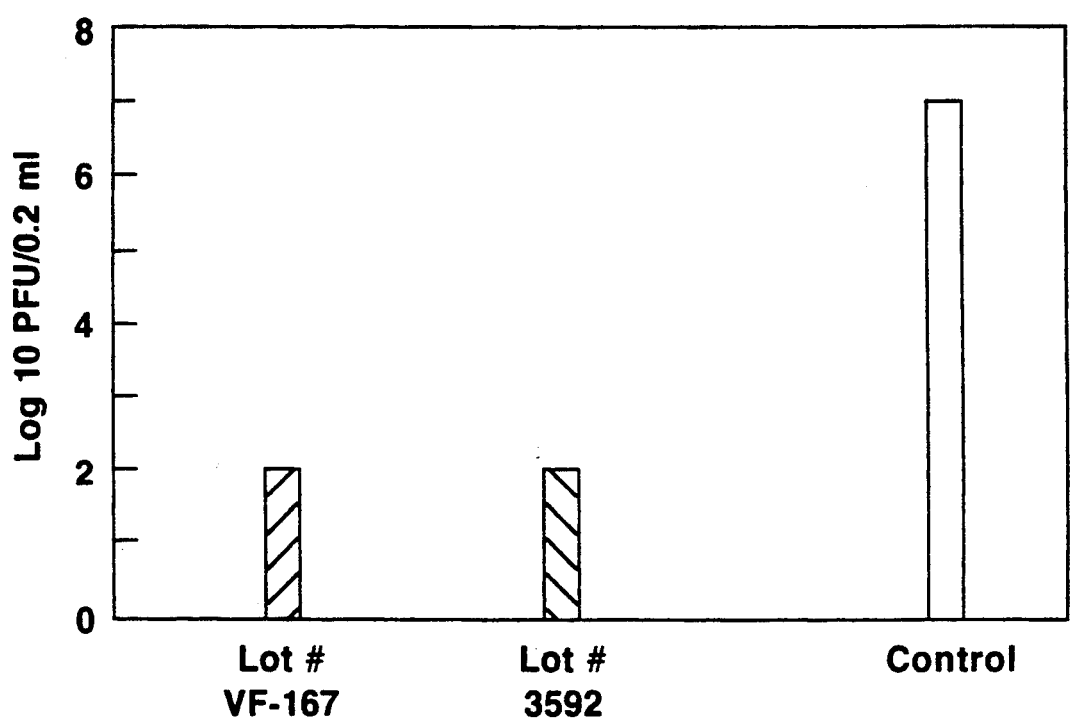
FIG. 1 presents data showing that, over a range of dilutions, the composition of the present invention prevents the attachment of at least 5 logs of Herpes virus to the cells in culture.

The compositions of the present invention is composed of a carrier, licorice root extract, tannic acid, chondrus extract, and water.

The carrier component is physiologically compatible with human skin and membrane tissues. The carrier may be a mixture of components. It is non-irritating and typically acts as a thickening agent for the composition: a number of such agents are well known in the art see, for example, the CTFA Cosmetic Ingredient Dictionary. Carrier components may also act as a solvent for other components of the composition. In addition the carrier may act as a demulcent and may have emollient properties. Some typical carrier components include glycerin and pectin. Glycerin is a viscous hygroscopic liquid which acts as a solvent and demulcent. In the formulation of the present invention, glycerin is typically present at a concentration of 15-40% v/v: concentrations of glycerin may be varied to achieved over an even broader range to achieve a desired consistency. A second carrier component used in the present invention is pectin. Pectin is a negatively charged polysaccharide that adds viscosity to the composition of the present invention. Typically, pectin is included at a concentration of 0.5% to 2% w/v: however, as for glycerin above, the concentration may be considerably varied to achieve a desired consistency. Other typical carrier components include gums, mucilages, dextrins, hydroxy- and carboxycelluloses. Carrier components may be added which provide (i) an agreeable feeling (such as camphor or phenol), (ii) improved fluidity (such as polyalcohols), and (iii) improved storage stability (such as sodium benzoate).

The composition of the present invention also includes licorice root extract. Licorice root extract can be obtained by a number of well-established procedures (Nieman, K., 1952). The extraction procedures are such that the glycyrrhizin concentration of the extract is about 16-18%. Licorice root extract obtained from *Glycyrrhiaglabra linné*. (Spanish licorice) or *Glycyrrhiaglabra linné var. glandulifera* (Russian licorice) can be purchased from a number of sources including Meer Corporation, North Bergen, NJ 07047. For convenience Spanish licorice extract was used in this composition. Preferred embodiments of the present invention include licorice root extract at between about 0.025% and 0.75% w/v.

The composition of the invention further includes a condensed tannin, such as tannic acid (Pratt, R., and Younken, H. W., 1956). Unlike prior art compositions that have high concentrations of tannic acid (see Background), the preferred range of tannic acid in the present composition is between about 0.8 and 1.5% w/v.

The final component of the present invention is carrageenan (or chondrus extract). Carrageenan is a coldwater soluble emulsifier consisting of sulfated polysaccharides. Carrageenan is obtained from red algae including *Rhodophyceae, Chondrus crispus, Gigartiana stellata*, and *Gigartinaceae*. The carrageenan used in the composition of the present invention can be in the form of an algal homogenate (Deig et al.), an algal extract (Example 1), or can be purchased from commercial sources (e.g., "VISCARIN," FMC, Marine Colloids Division, Philadelphia, Penna. 19103). The preferred concentration range of carrageenan in the composition of the present invention is between about 0.1 to 1.5% w/v.

A number of preservatives are available for use in the composition of the present invention including: benzalkonium chloride, organic mercury compounds, sorbic acid, hexachlorophene, and parabens. One preferred preservative is sodium benzoate at a concentration of about 0.25% w/v.

The above ranges of concentration provide preferred concentrations to guide one of ordinary skill in the art: however, concentrations of the components may be modified and the resulting composition tested for efficacy, for example, as described in Example 3.

Example 2 describes a preferred formulation of the present invention where the composition consists of the following components: glycerin, 20% v/v; pectin, 1.0% w/v; licorice root extract, 0.025% w/v; tannic acid, 1.0% w/v; "VISCARIN GP269," 0.1% w/v; sodium benzoate, 0.25% w/v; and distilled water.

II. Methods of Using the Present Composition

The anti-viral properties of the composition of the present invention were examined (Example 3). The formulation described in Example 2 was diluted 1:6 in Minimal Essential Medium and applied to Vero Monkey Kidney cells two hours before and simultaneously with a viral challenge of Herpes simplex I virus (Mahoney strain). Cytopathogenic effect on the cells were observed for 5 days. As can be seen from the results of this test, presented in FIG. 1, in dilute concentrations the formulation of the present invention significantly prevented the attachment of at least 5 Logs (100,000) of Herpes virus to the tissue culture cells. Similar results were obtained with Herpes simplex II, the genital herpes virus.

The preferred method of treatment of the present invention is to apply a quantity of the composition sufficient to cover the affected area. This may be by spray or application with cotton swab or soaked gauze. For minor skin abrasions and bites one application is usually all that is necessary to relieve pain and scratching. The composition of the present invention may also be applied in other pharmacologically acceptable carrier media such as creams and gels (Remington's Pharmaceutical Sciences, 1975).

For herpetic lesions the mixture is applied, for example, using a cotton pad held to the lesion for 7-9 minutes at which time pain is relieved. Subsequently, the mixture can be applied several times per day until the lesion resolves.

The formulation described in Example 2 was tested in vivo on numerous human patients. The formulation was tested under the supervision of a physician. Short case histories and comments are presented in Example 4. As can be seen from these case histories the composition of the present invention is useful in treating a wide variety of viral and inflammatory skin disorders including: Herpes Zoster, bee stings, bug bites, eczema, psoriasis, apthos ulcers/canker sores, oral/labial herpes, genital herpes, pharyngitis/tonsillitis, and dermatitis.

III. Utility

The present invention provides a composition comprising tannic acid, licorice root, and carrageenan, which is useful for the treatment of a number of skin disorders: the present invention also describes methods of use for this composition.

One embodiment of the present invention is a method of treating cold sores. Cold sores (fever blisters) are common names for the acute infectious disease caused by the virus Herpes simplex I. The usual site of the sore is at the junction of the mucous membrane and skin on the lips or nose. Sores can occur on other parts of the body including the genital area, but typically genital infections are caused by the Herpes simplex virus Type II. The cold sore virus is spread from person to person by the oral or respiratory route whereas the genital herpes virus is spread by sexual contact.

The composition of the present invention is a topical protectant and provides relief of discomfort due to cold sores. The combination of ingredients softens and soothes the cold sore, preventing cracking, and is most effective when the recurrent herpes infection just begins (mild burning and itching).

The present composition can also be applied in a similar manner to skin irritations due to chapping, sunburn, windburn, scrapes, abrasions, or cracked lips. As with most medications, a physician should be consulted for any lesion or inflammation that persists for more than one week.

The following examples illustrate, but in no way are intended to limit the present invention.

MATERIALS AND METHODS

Glycerin was obtained from Fisher Scientific, Fair Lawn, N.Y., 07301. Pectin was obtained from Kodak, Rochester, N.Y., 14650. Tannic acid was purchased from Sigma, St. Louis, Mo., 63178. Sodium benzoate was obtained from Fisher Scientific, Rochester, N.Y., 14650. Licorice root extract was purchased from Meer Corporation. Carrageenan was purchased as "VISCARIN" from Marine Colloids.

Example 1

Chondrus Extract

Algal Extracts containing carrageenans can be prepared as follows.

Prior to extraction, each frozen algal sample is combined with citrate phosphate buffer (0.07 M citric acid, 0.15 M $Na_2HPO$) at pH 7.0 to make a 20% net wt vol mixture. The mixture is homogenized at room temperature in a large Waring blender and left overnight at 4° C. The suspended homogenate (primary aqueous homogenate) is then centrifuged (10,000 rpm, 5 minutes) and the supernatant (primary aqueous extract) is used for antiviral activity (Ehresmann et al.).

Two methods can be used to isolate and partially purify viral interfering substance from algae (Ehresmann et al.) In method I, whole algal thalli of, for example, *Constantinea simplex* Setchell are extracted for large molecular weight polysaccharides by a modification of the procedure of Su et al. Specimens of the algae (net weight 121 g) are washed 3X with sterile distilled water, drained, dried and place in 100 ml boiling ethanol. The mixture is returned to boiling for 2 minutes and immediately homogenized in a Waring blender until the thalli disintegrate. 160 ml 95% ethanol are added to the suspension and the mixture quickly brought to 65° C. After 5 minutes at 65° C. the mixture is returned to room temperature and filtered through Whatman #1 paper. The cellular residue (18 g) is then dried overnight and added to 300 ml sterile distilled water heated to 80° C. Extraction is facilitated by constant stirring and can be maintained at 80° C. for 2 h. Two volumes 95% ethanol are added to the supernatant obtained after centrifugation (10,000 rpm, 5 minutes) of the viscous extract. The resulting precipitate is washed 3X with ethanol, dried, weighed, dissolved in citrate phosphate or other suitable buffer. Such preparations can be analyzed for antiviral activity as described in Example 3.

In method II, 10 ml of a primary aqueous homogenate of, for example, *Farlowia mollis*, is sonicated 30 minutes and extracted with an equal volume of liquidated phenol at room temperature for 10 minutes after vigorous mixing. The emulsion is broken by centrifugation (5,000 rpm, 5 minutes) after which the aqueous phase is carefully removed. Polysaccharides and nucleic acids are precipitated by addition to the aqueous phase of 2 vol cold 95% ethanol. Removal of phenol from the precipitate is facilitated by 2 cycles of dissolution in water and precipitation by ethanol. Finally the precipitate is then dried, weighed, and dissolved in a suitable buffer.

Measurements can be performed to determine the chemical nature of the antiviral substance in extracts of active algae by standard analysis procedures, such as UV spectrophotometry, molecular sieving, and protein and polysaccharide quantification.

EXAMPLE 2

Formulation of the Composition of the Present Invention

This example describes a typical formulation using the components described above in Section I.

Glycerin, pectin, and sodium benzoate are added to deionized water with stirring for one hour at room temperature. Tannic acid and licorice room extract are then added with vigorous stirring. After about 30 minutes the "VISCARIN" is added very slowly with vigorous stirring. Solubilization occurs in about one hour.

EXAMPLE 3

In vitro Anti-viral Activity

Vera Monkey Kidney (VMK) Cells (American Type Culture Collection ATCC-CRL 1586 VerC1008) were cultured by standard procedures (Deig et al., 1974).

The composition described in Example 2 was diluted 1:6 in minimal essential medium (Gibco-BRL, Gaithersburg Md.) and applied to the VMK cells in a 1 ml volume for either (i) two hours before or (ii) simultaneously with Herpes virus challenge. The virus challenge consisted of approximately $1 \times 10^7$ Herpes simplex 1 (Mahoney strain, California State Department of Health Laboratory collection).

Cytopathogenic effects on the cells were observed for 5 days. The results in Figure 1 show the testing of two lots of the composition described in Example 2 versus an untreated control. The left axis shows the $\log_{10}$ plaque forming units per 0.2 ml of virus ($1 \times 10^7$ infectious virus, see control) and the bottom axis shows the sample tested. These results indicate that the composition of the present invention, even at a 1:6 dilution, prevented the attachment to culture cells of at least 5 logs of Herpes virus, relative to the control. Similar results were obtained with Herpes Simplex II (Strain Johnson, California State Department of Health Laboratory collection).

EXAMPLE 4

Short Case Presentations

This example presents short case presentations for a number of viral and other skin disorders treated with the formulation described in Example 2. Typically, the composition of the present invention was delivered by pump spray to cover the affected area.

A. HERPES ZOSTER

B.H., a 73 year old female, noted four day-old rash on back. She had suffered a recent myocardial infarction eight days prior to presentation. She has refused "to take any more medicine". Her vesicular lesions were diagnosed as Herpes zoster along right buttock, about 7×3 cm in area. The formulation was applied by pump spray and the patient stated she was pain free within 10 minutes.

A 67 year old female (M.C.) presented with less than 2 cm patch of typical *H. zoster* lesions beneath the left breast which was "burning". The formulation was applied and the patient was denied any discomfort by five minutes.

M.F. was a 31 year old female who complained of "pain and swelling" along right side of her rib cage. It had not responded to a popular cream. The physician diagnosed *H. zoster* (shingles) and sprayed the lesions. All discomfort ceased within 7 minutes.

N.P. used over-the-counter methods of pain relief with no relief from shingles involving the right side of the thorax at thoracic vertebral levels 10 and 11. A physician began her with a steroid injection and a course of acyclovir by mouth. She returned the next day to the clinic where another physician sprayed on the formulation. All pain ceased within 2 minutes and lasted over 5 hours.

M.C. appeared in clinic with a large swath of *H. zoster* in full eruption on the right lower back. Typically, none of the vesicles or erythema crossed the midline. The patient was quite uncomfortable. An experienced physician diagnosed *H. zoster* and applied the formulation. The patient reported "75% of the pain, burning and itch" gone in 5 minutes. Ten minutes elapsed before total resolution of discomfort.

66 year old G.C. complained of "spider bites" on the posterior scalp. The pain had begun "3 or 4 days ago". A diagnosis of *H. zoster* in eruption was made. The formulation was applied and the patient was pain free in less than 5 minutes. Relief lasted greater than 4 hours. The lesions were gone on return visit in 2 days.

A 12 year old female (A.N.) was diagnosed with *H. zoster* on the left shoulder. The 2 cm lesion was of several vesicles over an erythematous base and was extremely painful to touch. *H. zoster* was diagnosed by standard methods. The child was pain free with the lesions now palpable without pain in less than 10 minutes.

B. BEE STINGS

F.P., a 75 year old woman, was stung by a bee 24 hours before presentation. The puncture wound was noted on the third digit of the left hand and the patient complained of an inflamed area and pain which "radiates up my arm". The health care provider notes "(the formula) applied with good relief in less than 5 minutes".

A 22 year old female presented with a 2 day old sting she acquired by stepping on a bee while barefoot. A 3 cm area of erythema was noted by the physician with attendant tenderness. Following application of the formula, the patient reported almost complete relief of pain in 5 minutes.

C. BUG BITES

A 5 year old female (E.F.) was noted to have scattered red itchy papules on her arm, right cheek and right eyelid. She was otherwise well. The lid was violaceous tender and "very itchy". The formula was applied to the closed eye by soaked gauze for five minutes. Following this period, the child reported "it feel much better". Itching was denied over one hour later and the swelling reported reduced.

A 48 year old female (S.J.) complained of insect bites to the back of the right knee three days prior. She reported continued itchiness and swelling. She had tried diphenhydramine with limited success. The spray formulation was applied and the patient was itch free in 3 minutes.

J.T. was a 24 year old female seen initially nine days before application of the formulation to her "mite" bites. No relief with antibiotics. She became itch and pain free within 7 minutes of application. Repeated use followed after several hours.

D. PHARYNGITIS/TONSILLITIS

C.S. was a 44 year old male who complained of sore throat for 24 hours. His streptococcal culture proved negative and viral pharyngitis was diagnosed. The pain relief was complete and laster after a 1 minute gargle with the formulation.

M.M., a 61 year old female, complained of left ear pain, dizziness and sore throat not getting better and totally unresponsive to home remedies. She had been suffering for 3 weeks. She gargled with 10 cc of the formulation for 2 minutes and obtained complete relief in 5 minutes. Her comment: "it works great!"

H.R., 43, complained of a "severe sore throat and achy body" for 2½ weeks. He had self treated with antibiotics without success. He was reportedly quite fatigued. An experienced physician diagnosed viral syndrome with viral pharyngitis. After appropriate lab tests the diagnosis was *mononucleosis pharyngitis*. Gargling with the formulation resolved all throat pain in 2 minutes.

L.B. had a sore throat for 4 days with over-the-counter medications failing, including acetaminophen. Examination revealed a herpetic lip lesion, the strep test was negative. Viral tonsillitis was diagnosed. There was a complete resolution of all discomfort after application of the formula to the lip and a 1 minute gargle.

E. DERMATITIS

M.C., a 58 year old female, stated she is "allergic to canines of all types", among other things. She complained of "very itchy hives" and demonstrated multiple weal and flare reactions typical of a systemic allergic response. The formulation was applied by spraying and the rash was noted to be fading slightly and to be totally itch free by 5 minutes.

Following prolonged exposure to the sun, patient C.W., a nurse, reported "itching and stinging" to her back. One minute following spraying on of the formula, all discomfort was gone and relief "lasted for hours".

P.S., a 50 year old female, was diagnosed with "burning" on the chest and back. Her physician diagnosed erythema multiform and applied the formulation. She reported relief "in 10 seconds" which lasted "as long as the (formulation) was on my skin".

25 year old C.H. complained of large hives over arms, chest and back. The formula was applied to the right arm only. It became itch free in 3 minutes.

T.E., a 52 year old female with a long list of allergies, presented with a "itchy rash on both arms and legs for 3 or 4 days". Idiopathic allergic reaction was the diagnosis. Total itch relief was found in 3 minutes.

F. ECZEMA

M.W. was a 25 year old, 2 month pregnant, atopic female with total body eczema. She has suspended painful "allergy shots" and "steroid shots" for the duration of the pregnancy. Antihistamine tablets were refused by the patient secondary to drowsiness. She presented with total body itch. The formulation was liberally sprayed over the left side of the body with relief in 2 minutes. The remainder of the body was then treated. The patient reported on follow up that relief lasted 2½ hours with one application.

H.T. was a 21 year old female with significant eczema. She presented with several eczemoid patches on the forehead and nasal area. "I am ready to pull my hair out!" due to discomfort, she stated. The formulation was applied and total relief was found in 1 minute.

G. APTHOS ULCERS/CANKER SORES

D.C., 32, found "blisters" in her throat two days prior to presentation. She was diagnosed with viral induced apthos ulcers of the posterior pharynx which were painful enough to keep her from eating. A 1 minute gargle with the formulation produced complete pain relief for 1 hour. Repeat application showed longer relief K.T. is a 17 year old male presented with a large flat ulcer under the tongue which was painful to touch with a tongue blade. Approximately 1 cc of the formula was placed on a cotton ball and held against the lesion for 7 minutes. The lesion became pain free to touch after this time. The patient denied any anesthesia feeling to the healthy surrounding tissue.

A 52 year old female (M.B.) came to the clinic, claiming she was "feverish". She also complained of body aches, mouth pain producing drooling and a nasal discharge. On oral inspection 4 or 5 plaque-like lesions were seen on the inner lower lip and buccal mucosa. Cotton soaked formulation held in place for 7 minutes completely eliminated the pain.

K.D. was 2 when she presented with complaint of "pain and swelling inside of mouth through cheek to ear with headache and bad taste" in the mouth. Two obvious canker sores were detected, bathed for 5 minutes with the formulation and touched without pain thereafter. Viral cultures yielded HSV-1.

S.A. was a 44 year old female complaining of "difficulty swallowing for the past 5 days". She also had "swollen glands for 3 days, with a 3 day headache and temperature to 103 degrees". Examination revealed a viral clinical picture with severe and extensive apthos ulcers throughout the mouth which were very painful to touch. Following holding the formulation as to bathe the lesions for 3 minutes she was pain free in 10 minutes.

H. PSORIASIS

M.M. is a 33 year old nurse with many years of psoriasis by history. On one occasion after having been supplied with the formulation she "awoke with my psoriasis on elbows . . . flared up—red, sore and itchy". She sprayed (the formulation) on them and got fast relief —within 2 minutes, and "it lasted the entire day!".

R.M. is a 62 year old female nurse with diagnosed lichen planus for which she has been using 1% cortisone. She used the formulation and obtained significant relief of symptoms of itching and burning in seconds which lasted "for hours".

I. ORAL LABIAL HERPES

E.G. is a 24 year old female who came to the clinic complaining of a "tingling sensation" to the lower lip for 1 month. On the day of visit, the lip erupted with a single painful, fluid-filled vesicle. The formulation relieved the pain and tingling in less than 10 minutes. Cultures proved HSV-1.

P.P. is a 25 year old female with a "cold sore" on the lower lip. She had begun acyclovir for a few but couldn't wait for the pain relief it might bring. Direct application of the formulation for 5 minutes gave significant relief which was total in 10 minutes. The pain relief lasted 1-2 hours according to the patient.

R.S. was a 26 year old male who attributes his labial cold sores to "sun and stress". The noted the lesion the night before presentation. The formulation, applied by a soaked cotton ball, rendered him completely pain free in 2-3 minutes.

J. GENITAL HERPES

S.S., a 26 year old female, noted inguinal swelling and tenderness for three days. Examination revealed several clustered vesicles which proved to be HSV-2 lesions on culture. Spraying on of the formula proved to be pain relieving in 7 minutes.

A.B. was a 25 year old male who noted "severe pain in the left groin" with "little bumps" at the base of the penis. Cultures proved to be positive for HSV-2. The patient was sprayed with the formulation and was pain free at the lesion site in 5 minutes.

G.P. A 41 year old female states she "maybe has herpes". "I have small, red, irritated bumps on the labia which are very painful". The patient was in severe distress and could not walk upright due to pain. The formulation saturated the area and the patient was pain free in 10 minutes. Cultures proved HSV-2.

K.G. was a 30 year old male who stated he "broke out with fluid-filled blisters on face, arms, and legs 3 days ago. Some are scabbed over now. More recently I have new fluid-filled blisters on my back." Examination reveals a 4 inch swath along the right side of the thorax from spine to mid-abdomen following the sensory dermatome. The diagnosis was *H. zoster*, classic. The formulation was sprayed on and all pain was gone in 10 minutes.

While the invention has been described with reference to specific methods and embodiments, it will be appreciated that various modifications and changes may be made without departing from the invention.

It is claimed:

1. A composition suitable for providing a topical dermatological spray comprising
   tannic acid, licorice root extract, carrageenan, and a pharmacologically acceptable fluid carrier,
   wherein the concentration of tannic acid is in the range of approximately 0.8% to 1.5% w/v, licorice root extract is in the range of approximately 0.025% to 0.75% w/v, and carrageenan is in the range of approximately 0.1% to 1.5% w/v.

2. The composition of claim 1, wherein the fluid vehicle comprises glycerin and pectin.

3. The composition of claim 1, wherein the fluid vehicle further contains a preservative.

4. The composition of claim 3, wherein said preservative is sodium benzoate.

5. The composition of claim 4 wherein the fluid vehicle comprises glycerin and pectin.

6. The composition of claim 5, consisting essentially of glycerin, 20% v/v; pectin, 1.0% w/v; licorice root extract, 0.025% w/v; tannic acid, 1.0% w/v; carrageenan, 0.1% w/v; sodium benzoate, 0.25% w/v; and distilled water.

7. A method of treating skin disorders and inflammations for a subject in need of treatment, comprising topical application of a pharmacologically effective amount of a composition comprising tannic acid, licorice root extract, carrageenan, and a pharmacologically acceptable fluid carrier, wherein the concentration of tannic acid is in the range of approximately 0.8% to 1.5% w/v, licorice root extract is in the range of approximately 0.025% to 0.75% w/v, and carrageenan is in the range of approximately 0.1% to 1.5% w/v.

8. The method of claim 7, wherein the fluid vehicle comprises glycerin and pectin.

9. The method of claim 7, wherein the fluid vehicle further contains a preservative.

10. The method of claim 1, wherein said preservative is sodium benzoate.

11. The method of claim 10 wherein the fluid vehicle comprises glycerin and pectin.

12. The method of claim 7, for the treatment of herptes virus infection.

13. The method of claim 11, wherein the composition consists essentially of glycerin, 20% v/v; pectin, 1.0% w/v; licorice root extract, 0.025% w/v; tannic acid, 1.0% w/v; carrageenan, 0.1% w/v; sodium benzoate, 0.25% w/v; and distilled water.

* * * * *